(12) United States Patent
Williams

(10) Patent No.: US 10,624,624 B2
(45) Date of Patent: Apr. 21, 2020

(54) TECHNIQUE AND SYSTEM FOR LATERAL LUMBAR SPINE FUSION

(71) Applicant: Seth K. Williams, Madison, WI (US)

(72) Inventor: Seth K. Williams, Madison, WI (US)

(73) Assignee: Seth K. Williams, Madison, WI (US)

( * ) Notice: Subject to any disclaimer, the term of this patent is extended or adjusted under 35 U.S.C. 154(b) by 50 days.

(21) Appl. No.: 15/907,578

(22) Filed: Feb. 28, 2018

(65) Prior Publication Data

US 2018/0185016 A1 Jul. 5, 2018

Related U.S. Application Data

(63) Continuation of application No. 15/090,015, filed on Apr. 4, 2016, now Pat. No. 9,924,932.

(60) Provisional application No. 62/261,525, filed on Dec. 1, 2015.

(51) Int. Cl.
| | | |
|---|---|---|
| *A61B 17/02* | (2006.01) | |
| *A61B 5/0488* | (2006.01) | |
| *A61B 5/00* | (2006.01) | |
| *A61B 90/00* | (2016.01) | |

(52) U.S. Cl.
CPC .......... *A61B 17/025* (2013.01); *A61B 5/0488* (2013.01); *A61B 5/4893* (2013.01); *A61B 5/6847* (2013.01); *A61B 2017/0256* (2013.01); *A61B 2017/0262* (2013.01); *A61B 2090/036* (2016.02); *A61B 2505/05* (2013.01)

(58) Field of Classification Search
CPC combination set(s) only.
See application file for complete search history.

(56) References Cited

U.S. PATENT DOCUMENTS

| | | | | |
|---|---|---|---|---|
| 8,636,655 | B1* | 1/2014 | Childs | A61B 17/0206 600/219 |
| 8,974,381 | B1* | 3/2015 | Lovell | A61B 17/0206 600/232 |
| 9,044,280 | B1* | 6/2015 | Arambula | A61B 17/0206 |
| 9,700,293 | B2* | 7/2017 | Cryder | A61B 17/025 |
| 2005/0137461 | A1* | 6/2005 | Marchek | A61B 17/025 600/220 |
| 2006/0247645 | A1* | 11/2006 | Wilcox | A61B 17/025 606/86 R |
| 2011/0224497 | A1* | 9/2011 | Weiman | A61B 17/02 600/231 |
| 2014/0066718 | A1* | 3/2014 | Fiechter | A61B 17/0206 600/214 |
| 2016/0081818 | A1* | 3/2016 | Waugh | A61B 17/0206 623/17.16 |

* cited by examiner

*Primary Examiner* — Lynnsy M Summitt
(74) *Attorney, Agent, or Firm* — Bell & Manning, LLC; Christopher Kalafut

(57) ABSTRACT

A lumbar spine fusion system includes a probe and a retractor blade. The probe includes a shaft, a pointed tip, and a collar. The pointed tip is configured to puncture tissue in a disk space of a disk and anchor the probe to the tissue. The collar is configured to act as a stop to control a distance through which the shaft of the probe traverses the tissue. The retractor blade includes an end portion and a slot. The slot is configured to receive at least a portion of the shaft of the probe. At least a portion of the end portion is configured to rest upon one or more of the disk and the collar when the retractor blade is mounted on the probe.

13 Claims, 11 Drawing Sheets

TECHNIQUE AND SYSTEM FOR LATERAL LUMBAR SPINE FUSION

CROSS-REFERENCE TO RELATED APPLICATIONS

The present application is a Continuation application of U.S. patent application Ser. No. 15/090,015 filed on Apr. 4, 2016, which claims priority to U.S. Provisional Patent Application No. 62/261,525 filed on Dec. 1, 2015, the entire disclosures of which are hereby incorporated by reference herein.

BACKGROUND

The lumbar spine refers to the lower back, and is where a human's spinal column curves inward toward the abdomen. The lumbar spine, which typically starts five to six inches below the shoulder blades, connects with the thoracic spine at the top and the sacral spine at the bottom. A human lumbar spine typically includes 5 vertebrae, although some individuals have six vertebrae in their lumbar spine. There are several different conditions that can affect the lumbar spine and cause pain, including disk problems. A lumbar spine fusion can be used to help alleviate pain in some individuals who are suffering from disk problems and other ailments.

SUMMARY

An illustrative lumbar spine fusion system includes a probe and a retractor blade. The probe includes a shaft, a pointed tip, and a collar. The pointed tip is configured to puncture through the annulus of the disk and enter the tissue in a disk space and anchor the probe to the tissue. The collar is configured to act as a stop to control a distance through which the shaft of the probe traverses the tissue. The retractor blade includes an end portion and a slot. The slot is configured to receive at least a portion of the shaft of the probe. At least a portion of the end portion of the retractor blade is configured to rest upon one or more of the collar and the disk when the retractor blade is mounted on the probe.

An illustrative retractor blade attachment system includes a probe that includes a shaft and a pointed tip. The pointed tip is configured to puncture tissue in a disk space of a disk and anchor the probe to the tissue. The system also includes a retractor blade attachment. The retractor blade attachment includes a slot configured to receive at least a portion of the shaft of the probe. The retractor blade attachment also includes one or more connections configured to secure the retractor blade attachment to a retractor blade.

An illustrative method of accessing a spine fusion site includes making an incision. A probe that includes a shaft and a collar is inserted through the incision and into a disk space of a disk such that the probe is anchored to the disk space. The method also includes placing a slot of a retractor blade over at least a portion of the shaft of the probe such that at least a portion of an end portion of the retractor blade rests upon one or more of the collar and the disk.

The foregoing is a summary of the disclosure and thus by necessity contains simplifications, generalizations, and omissions of detail. Consequently, those skilled in the art will appreciate that the summary is illustrative only and is not intended to be in any way limiting. Other aspects, features, and advantages of the devices and/or processes described herein, as defined by the claims, will become apparent in the detailed description set forth herein and taken in conjunction with the accompanying drawings.

DETAILED DESCRIPTION

Figure 1:
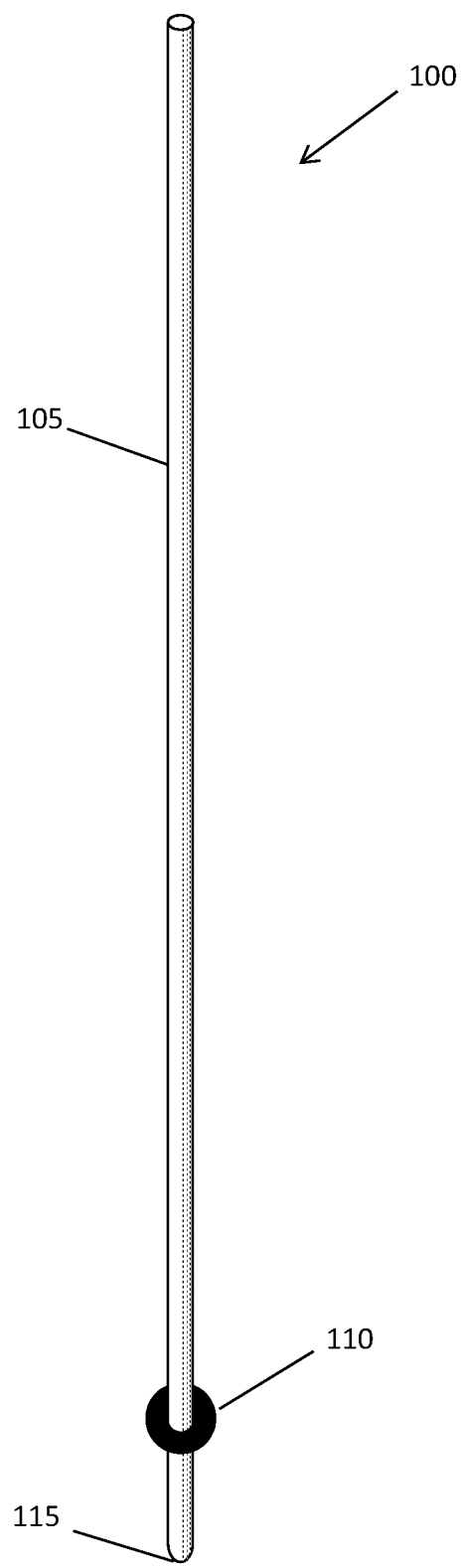
FIG. 1 depicts a probe in accordance with an illustrative embodiment.

Lateral lumbar spine fusion is typically performed through one or more incisions placed on the lateral aspect of the abdomen. The incision(s), which are made directly lateral to the vertebral column, are just big enough to accommodate a table-mounted expandable tubular retractor that allows visualization of the spine. The spine is approached through the retroperitoneal space. Once the retroperitoneal space is traversed, in order to visualize the spine, the operative corridor typically involves splitting the psoas muscle, which sits laterally to the left and right of the spinal column. This trans-psoas approach endangers the lumbar nerve plexus, which runs through the psoas muscle, and can also cause thigh pain due to irritation of the psoas muscle. Neurophysiological monitoring in the form of triggered electromyography (EMG) is used as an adjunct to the trans-psoas approach in order to identify nerves that lie within or near the surgical corridor so that the chance of nerve injury is minimized. A probe is typically placed through the psoas muscle and electrical current is applied via the probe in the standard fashion for triggered EMG. Provided the surgical corridor is deemed safe by the surgeon, serial dilators are placed, with triggered EMG performed after each dilator placement. Finally, a tubular table-mounted retractor is placed over the dilators so that the spine can be visualized.

An alternative retroperitoneal surgical technique involves a more oblique approach to the lumbar spine, working anterior to the psoas muscles rather than through the psoas muscle. This technique is less dependent on triggered EMG because the surgical corridor is anterior to the psoas muscle and the invested lumbar plexus. However, this procedure is a less direct approach to the spine and may endanger the blood vessels in the area.

Described herein are a system and technique that combine the benefits of a direct lateral retroperitoneal approach with a surgical corridor that is anterior to the psoas muscle. Such an approach minimizes or eliminates the need for triggered EMG, and reduces the number of steps needed to safely place the retractor. This technique and retractor design will expedite surgery at levels of the spine where the psoas muscle can be readily mobilized posteriorly. It will also save cost on surgeries in which neuromonitoring is not necessary. In addition, this technique and retractor can be used for lateral fusion in the thoracic spine, where the psoas muscle and lumbar plexus are not a factor.

One of the difficulties with current state-of-the-art lateral fusion approaches is the surgeon's ability to hold the dilators in the proper position on the disk space and then deploy the retractor over the dilators. It is common for the dilators to migrate during serial dilation and retractor placement. The technique and retractor here described solves this issue because the probe is anchored into a desired location in the disk space. Once the probe is anchored into the proper position, the retractor can immediately be placed (i.e., without the use of dilators), and will be in the desired position because the probe is already anchored. Placing the anchor probe as the first step also solves the problem of the psoas muscle migrating anteriorly, as commonly occurs when a dilator is placed without an anchor probe.

Another difficulty with current systems is the use of a deployable shim in the posterior blade of a retractor system that can be deployed into the disk space to anchor it in place. A concern with deploying this shim is the concern for it causing nerve damage. Instead of using a shim, the technique and retractor described herein involves placing the probe into the disk space under direct visualization, and with the option of using triggered EMG if it is thought this will be helpful. This probe then serves as the anchor over which the retractor is placed. As a result, anchoring the retractor with a device in the disk space is more readily and more safely accomplished using the embodiments described herein.

The approaches described herein take advantage of the smaller diameter of the psoas muscle and fewer lumbar plexus nerves at the upper lumbar levels, especially T12-L1, L1-L2, and L2-L3, occasionally L3-L4, and rarely L4-L5. The approaches described herein can also be applied to the thoracic spine, where the psoas muscle is not present. Images such as magnetic resonance imaging (MRI) images or computerized tomography (CT) images are studied to determine the size and location of the psoas muscle at the desired surgical level, and if it is felt that the anatomy is appropriate, this approach can be used. The present approach is performed through the same incision or incisions that would be utilized for a lateral retroperitoneal approach to the spine.

Once the anterior border of the psoas muscle is identified and the disk space identified on intra-operative imaging, the psoas muscle is carefully mobilized posteriorly to identify the disk space. A handheld retractor can be used to carefully retract the psoas muscle in its entirety posteriorly to further expose the disk space. A probe is then placed into the desired location in the disk space based on direct visualization and intra-operative imaging. The desired location is typically located in the posterior $1/3$ of the disk space, and will be located entirely or predominantly anterior to the psoas muscle. The probe will hold the psoas muscle posterior to the probe, setting up the later step of placing the retractor in a position that holds the psoas muscle entirely or predominantly posterior to the posterior retractor blade.

The lateral approach is designed for use with neuromonitoring, but this is likely not necessary at the upper lumbar levels because the psoas is smaller in diameter and contains fewer nerves, and the nerves are therefore less prone to injury. Thus the upper lumbar levels are more amenable to establishing a surgical corridor anterior to the psoas muscle. Depending on the individual patient anatomy, it may be possible to readily establish this corridor, placing the lumbar plexus at minimal risk. Under these circumstances, neuromonitoring likely does not provide any additional safety to the patient; instead it prolongs the procedure and may make it more complicated and even increase the risk of nerve injury if the retractor deployment time is prolonged. If the probe and retractor can safely be placed without neuromonitoring, the surgery will be more expeditious and involve fewer steps, and theoretically decrease the retractor deployment duration. Serial dilators will not need to be placed over the probe as is the standard protocol with current lateral lumbar fusion techniques. Instead, the retractor in its entirety can be placed along the probe immediately after the probe is anchored in the disk space.

FIG. 1 depicts a probe 100 in accordance with an illustrative embodiment. The probe 100 of FIG. 1 includes a shaft 105 having a circular cross section, and is composed primarily of metal. Alternatively, the probe may have an oval cross-section. A diameter of the probe 100 is approximately 2-3 mm, and the probe 100 is fairly rigid so that it can be manipulated manually and so that it can hold a retractor in place once the retractor is placed over the probe 100. In alternative embodiments, a different diameter of the probe may be used. The probe 100 also includes a collar 110 that is approximately 3-5 mm in diameter, although in alternative embodiments a smaller or larger diameter may be used. In an illustrative embodiment, the collar 110 is located approximately 15 cm from an end of the probe, and forms a pointed tip 115 of the probe 100 that can be inserted into tissue. The pointed tip 115 may be slightly blunted in order to avoid inadvertent injury to structures around the spine. In an alternative embodiment the tip 115 could include fixed or retractable teeth or flanges that would hold the probe 100 securely in the disk space. In such an embodiment in which the teeth or flanges are extendable and retractable, the extension/retraction can be performed by pushing a button on a handle or other portion of the probe. Upon pushing of the button, the teeth/flanges can be mechanically or electrically controlled, depending on the implementation. In an alternative embodiment the collar 110 may be closer to or further from an end of the probe, depending on patient's anatomy and surgeon preferences. In one embodiment, the collar is permanently fixed to a location along the shaft of the probe. In an alternative embodiment, the collar may be slidably fixed to the shaft of the probe. In such an embodiment, the collar may be secured to the probe shaft using a set screw or other fastener such that the collar can be slid to a desired location along the shaft. In an alternative embodiment, the probe can be designed without a collar.

The collar 110 functions to stop the probe 100 from advancing into the disk space beyond the collar 110. Specifically, the pointed tip 115 of the probe 100 is inserted into the disk space until the collar 110 contacts the lateral aspect of the disk and prevents further advancement of the probe 100. In another illustrative embodiment, the probe 100 can include an approximately 5 mm area above the collar 110 that is designed to conduct electrical stimulation so that triggered EMG can be employed through the probe 100 if desired. However, as discussed above, the embodiments described herein reduce or eliminate the need to use triggered EMG.

Once the probe 100 is anchored in the disk space and the appropriate position confirmed with direct visualization and via intra-operative imaging, a retractor blade with a circular or oval tube designed to accommodate and contain the probe is placed over the probe and slid down the probe onto the disk space. The psoas muscle is held posterior to the retractor blade, and the retractor blade is held in position by the probe that is itself anchored into the disk space. This retractor blade will typically be part of an expandable table-mounted retractor system that has a total of 2, 3 or 4 blades. The posterior blade is attached to the retractor system and then advanced along the probe, such that the probe, by nature of being anchored into the disk space and being contained within a tube in the retractor blade, holds the retractor in position. The retractor is therefore located anterior to the psoas muscle and holds the psoas muscle in position, thereby preventing it from migrating in an anterior direction. The table-mounted retractor is then secured to the operative table to lock it in position, the blades of the retractor are expanded to the desired diameter, and the spinal fusion proceeds in the standard manner. In alternative embodiment, the retractor blade can be used independently, without a table-mounted retractor system.

Figure 2A:
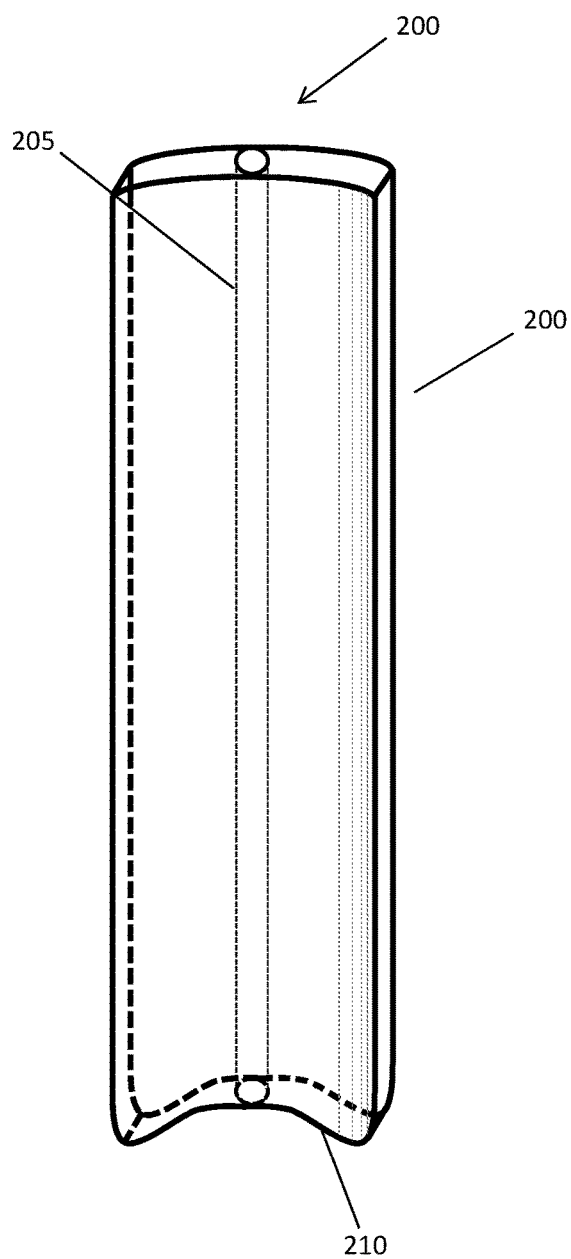
FIG. 2A depicts a retractor blade with a tubular slot and a concave end in accordance with an illustrative embodiment.
Figure 2B:
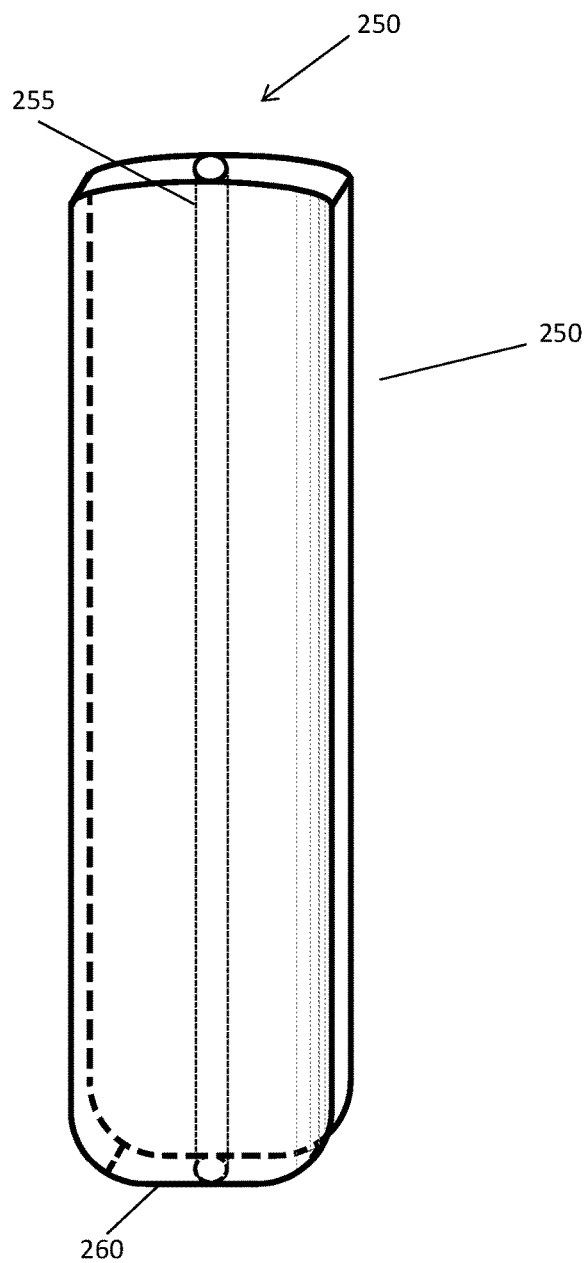
FIG. 2B depicts a retractor blade with a tubular slot and a convex end in accordance with an illustrative embodiment.

FIG. 2A depicts a retractor blade 200 with a tubular slot 205 and a concave end 210 in accordance with an illustrative embodiment. FIG. 2B depicts a retractor blade 250 with a tubular slot 255 and a convex end 260 in accordance with an illustrative embodiment. In alternative embodiments, the slots 205 and 255 may take on a shape other than tubular, such as triangular, square, etc. The tip of the retractor blade contacts and rests on the lateral aspect of the disk, and can be convex in nature as illustrated in FIG. 2B. Alternatively, the tip of the posterior retractor bade can be concave in shape with a variable radius of curvature to best accommodate the convex shape of the lateral aspect of the disk, as illustrated in FIG. 2A. In the embodiment of FIG. 2A, the concave end 210 of the retractor blade 200 would thus follow the shape of the disk and vertebral bodies, thereby preventing the psoas muscle from slipping underneath the corners of the retractor blade as can occur when the distal end of the retractor blade has a convex shape. The retractor blades described herein can be designed to be used with currently existing table-mounted retractors, or they can be part of a whole new table-mounted retractor design, or they can function independent of a table-mounted retractor system. The tip of the retractor blade can be flat rather than concave or convex.

Figure 3:
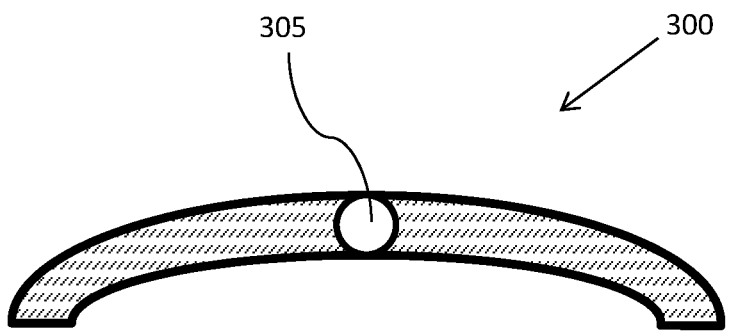
FIG. 3 is a cross-sectional view of a retractor blade in accordance with an illustrative embodiment.

FIG. 3 is a cross-sectional view of a retractor blade 300 in accordance with an illustrative embodiment. As illustrated in FIG. 2 and FIG. 3, a tubular slot 305 of the retractor blade 300 is positioned in-line with a wall of the retractor blade 300. Alternatively, the tubular slot 305 may be positioned at least partially internal to or external to the wall of the retractor blade.

Figure 4A:
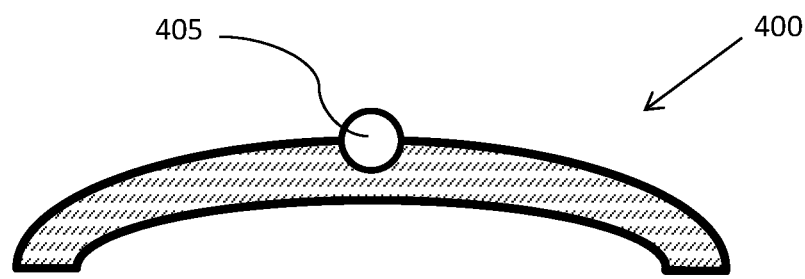
FIGS. 4A, 4B, 4C, and 4D are cross-sectional views of a retractor blade with the tubular slot in various configurations, in accordance with illustrative embodiments.

FIG. 4A is a cross sectional view of a retractor blade 400 in accordance with an illustrative embodiment. A tubular slot 405 is positioned eccentrically so that it is partially posterior to the retractor blade 400. Alternatively, the tubular slot may be positioned entirely posterior to the retractor blade.

Figure 4B:
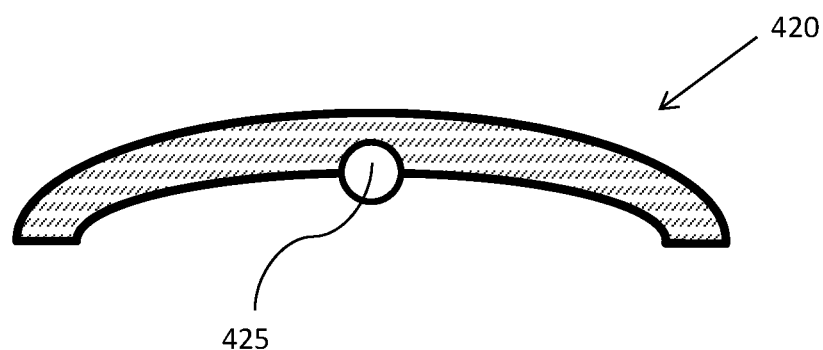

FIG. 4B is a cross sectional view of a retractor blade 420 in accordance with an illustrative embodiment. A tubular slot 425 is positioned eccentrically so that it is partially anterior to the retractor blade 420.

Figure 4C:
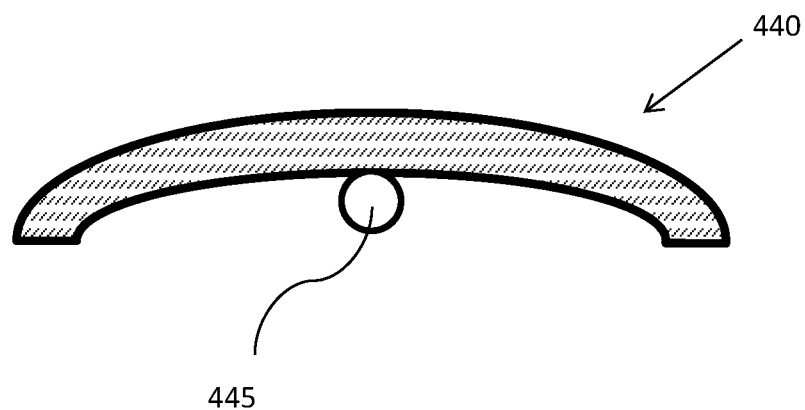

FIG. 4C is a cross sectional view of a retractor blade 440 in accordance with an illustrative embodiment. A tubular slot 445 is positioned entirely anterior to the retractor blade 440.

Figure 4D:
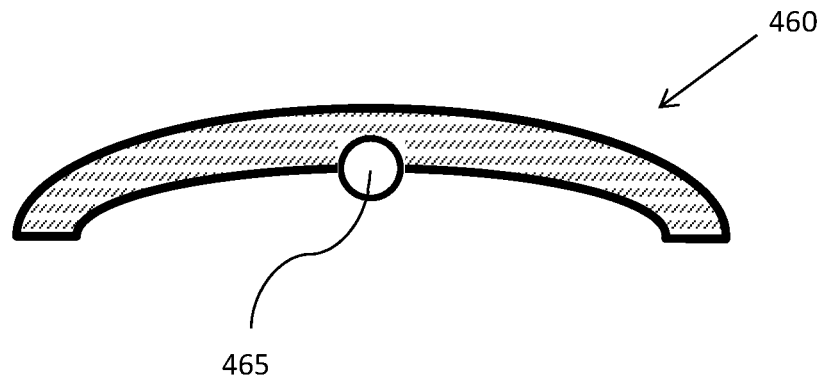
Figure 5:
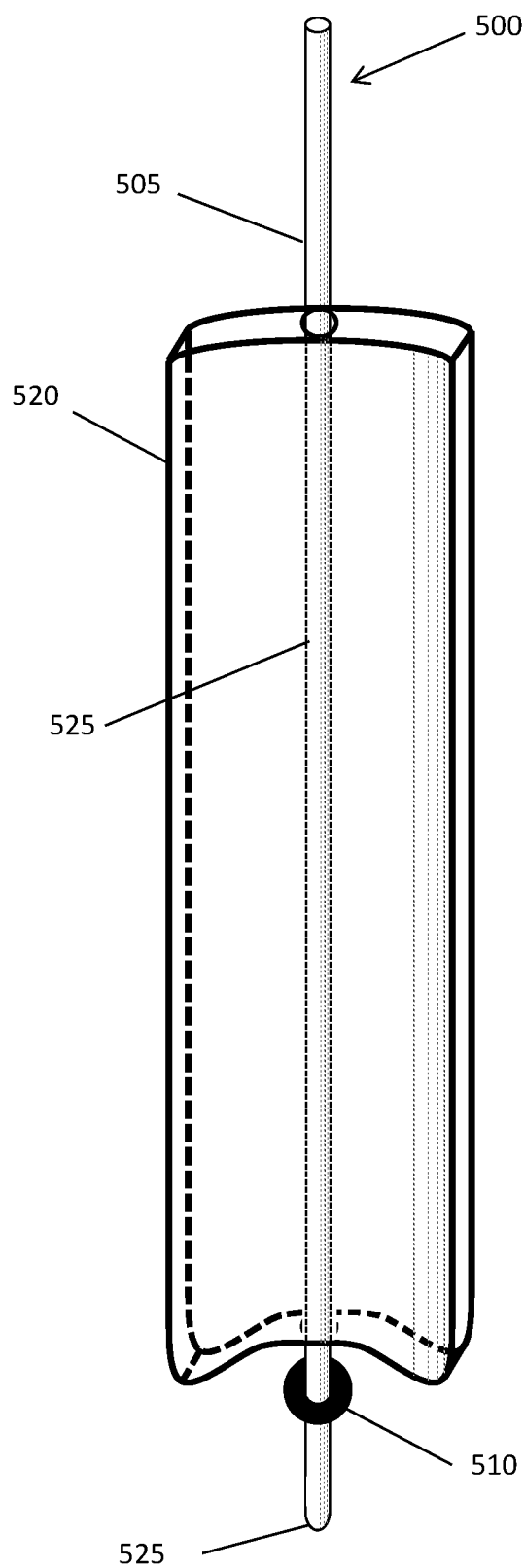
FIG. 5 depicts a retractor blade mounted on a probe in accordance with an illustrative embodiment.

FIG. 4D is a cross sectional view of a retractor blade 460 in accordance with an illustrative embodiment. A tubular slot 465 is positioned eccentrically so that it is partially anterior to the retractor blade, and the tubular slot 465 is partially open, unlike the embodiments in FIGS. 4A-4C. In alternative embodiments, any of the tubular slots 405, 425, and 445 of FIGS. 4A-4C may be partially open which would decrease its profile and facilitate cleaning the retractor blade slot after surgery FIG. 5 depicts a retractor blade 520 mounted on a probe 500 in accordance with an illustrative embodiment. Specifically, a tubular slot 525 of the retractor blade 520 is mounted onto a shaft 505 of the probe 500. A collar 510 of the probe 500 acts as a stop upon which a portion of an end of the retractor blade 520 rests. The collar 510 of the probe 500 also acts as a stop for insertion of a pointed tip 525 of the probe 500 into tissue. Specifically, the collar 510 controls a depth at which the probe 500 can be inserted into the tissue. In the embodiment of FIG. 5, the retractor blade 520 includes a convex end adjacent to the collar 510. As discussed above, in alternative embodiments, the end of the retractor blade may be concave such that the retractor blade better fits the contour of the disk upon which the retractor blade rests. It is also possible for the probe to not have a collar, in which case the tip of the retractor blade would contact the disk in its entirety rather that the collar.

Figures 6A, 6B:
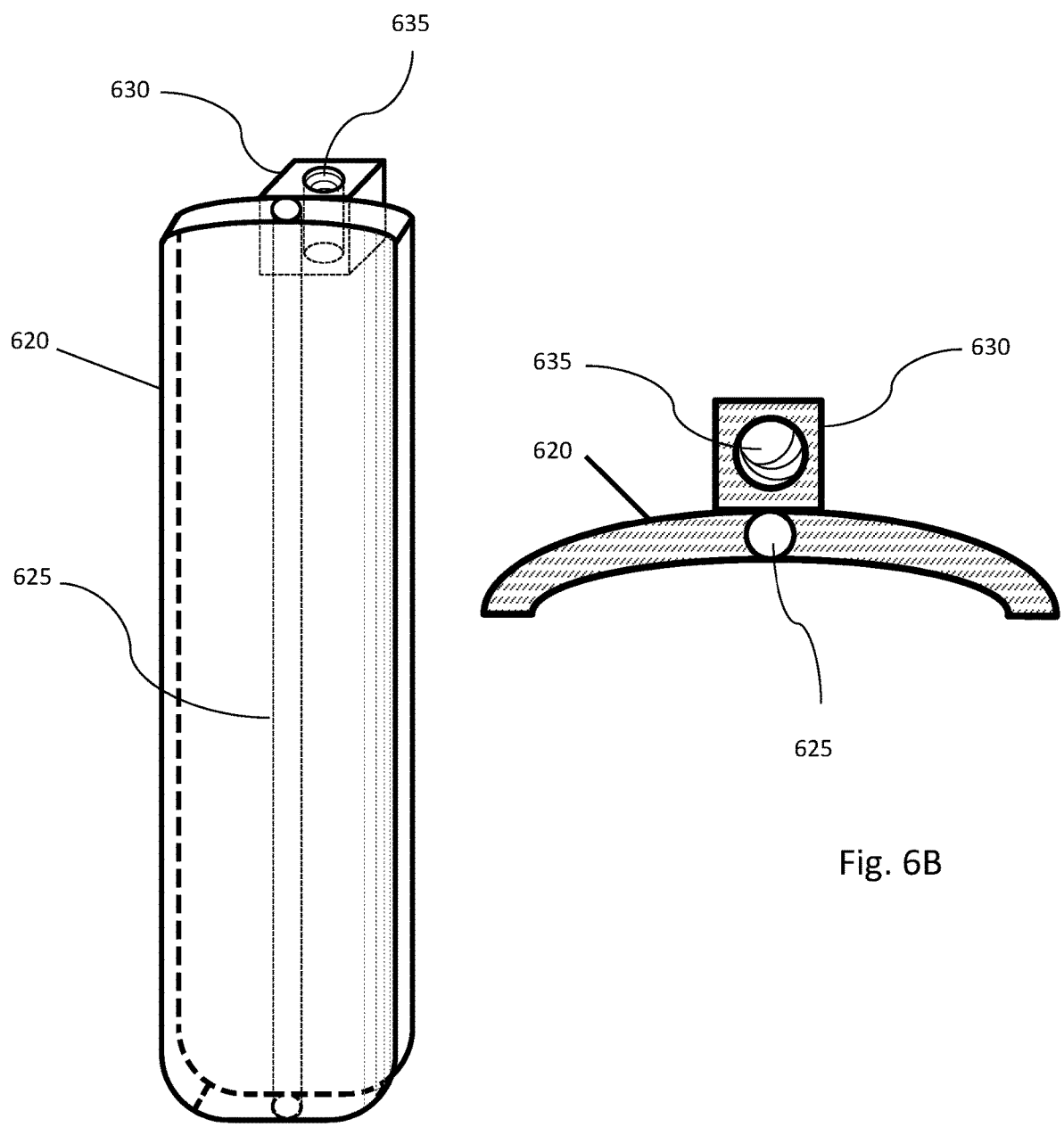
FIG. 6A depicts a retractor blade with an attachment for a handle or retractor system in accordance with an illustrative embodiment.
FIG. 6B is a cross-sectional view of a retractor blade with an attachment for a handle or retractor system in accordance with an illustrative embodiment.

FIG. 6A depicts a retractor blade 620 with a tubular slot 625 as described and referenced in FIG. 2B, with an attachment 630 designed to accommodate a handle that connects to the attachment 630 through an opening 635 in accordance with an illustrative embodiment. The opening 635 can be a threaded screw hole configured to receive a screw. Alternatively, the opening 635 can be configured to receive other attachment mechanisms such as a bolt, pin, clip, etc., and the opening 635 may be threaded or unthreaded depending on the embodiment. In another alternative embodiment, opening 635 can be used to secure the retractor blade 620 to an expandable retractor system.

FIG. 6B is a cross sectional view of a retractor blade 620 with a tubular slot 625 and an attachment 630 designed to connect to a handle or to an expandable retractor system through an opening 635. Similar to the embodiment of FIG. 6A, the opening 635 may be threaded or unthreaded, and can be configured to receive any of a number of different attachment mechanisms.

Figures 7A, 7B:
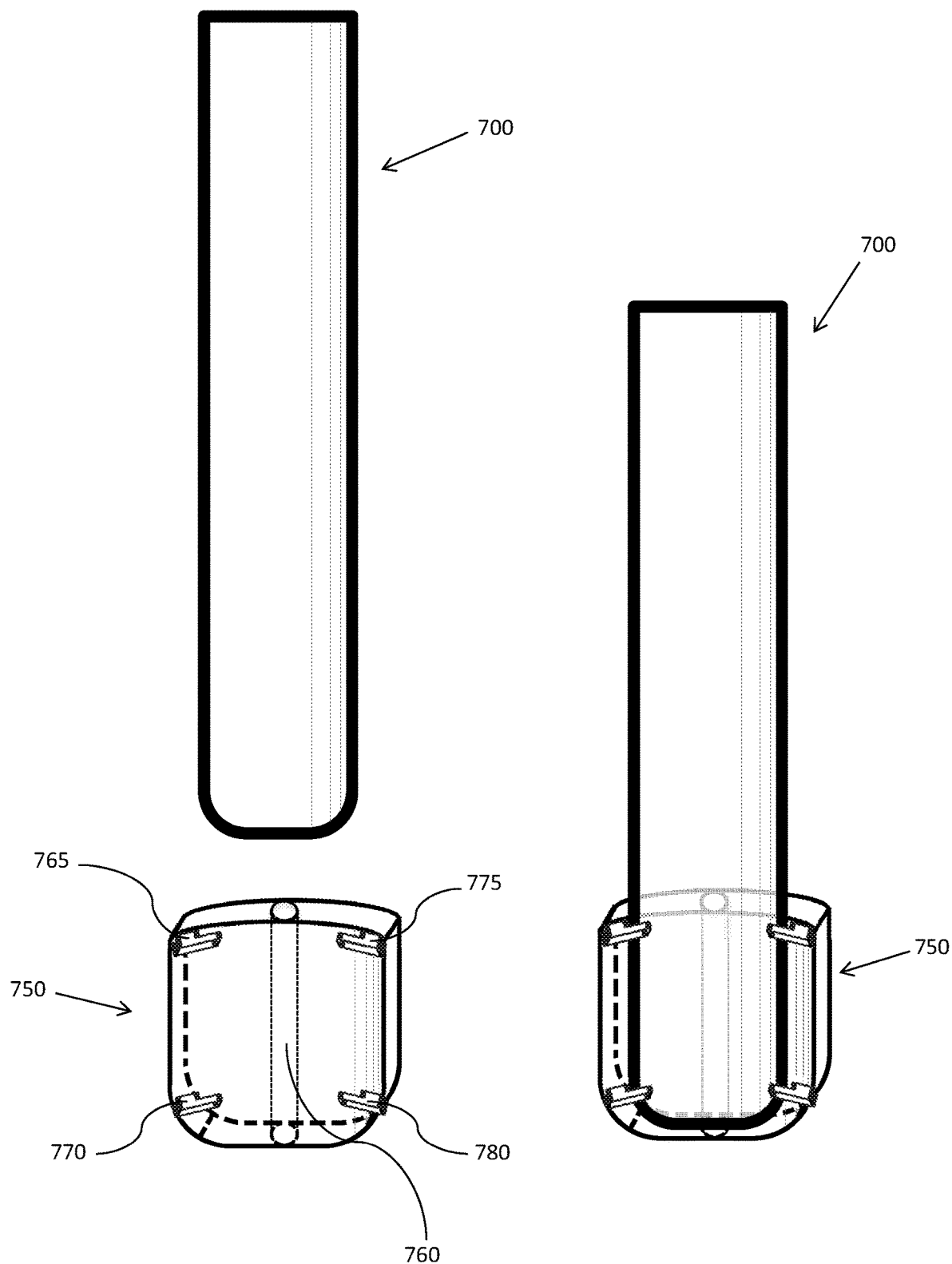
FIG. 7A depicts a shorter retractor blade with a tubular slot, that is designed to attach to a longer retractor blade that does not have a tubular slot in accordance with an illustrative embodiment.
FIG. 7B depicts a shorter retractor blade with a tubular slot, attached to a longer retractor blade that does not have a tubular slot in accordance with an illustrative embodiment.

FIG. 7A depicts a retractor blade 700 that does not have a tubular slot, but that slides into and connects to a retractor blade attachment 750 that has a tubular slot 760 in accordance with an illustrative embodiment. Retractor blade 700 attaches to retractor blade attachment 750 through connections 765, 770, 775, and 780, as depicted in FIG. 7B. In this embodiment, an existing retractor blade system that does not have a tubular slot can be used with retractor blade attachment 755 such that a probe as depicted in FIG. 1 is docked in the disk space and then the retractor blade 700 connected to retractor blade attachment 755 is slid along the probe through the tubular slot 760. The connections 765, 770, 775, and 780 are slotted clips that receive edges of the retractor blade 700 and hold the retractor blade 700 in place via a friction fit. In an alternative embodiment, retractor blade 700 can be joined to retractor blade attachment 750 through connection points other than 765, 770, 775, and 780. For example, fewer or additional connection points may be used. Also, other types of connections may be used, such as screw(s), bolt(s), spring loaded clips, detachable clips, etc.

Figure 8:
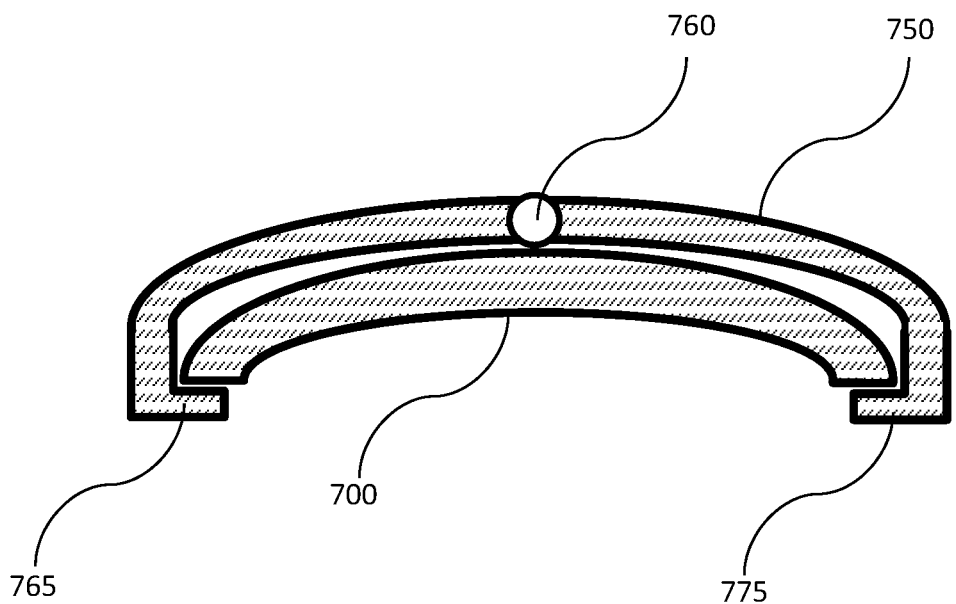
FIG. 8 is a cross-sectional view of a shorter retractor blade with a tubular slot, attached to a longer retractor blade that does not have a tubular slot in accordance with an illustrative embodiment.

FIG. 8 is a cross-sectional view of a retractor blade 700 secured to a retractor blade attachment 750 through connections 765 and 775. Retractor blade attachment 750 has a tubular slot 760. FIG. 8 is a cross-sectional view of FIG. 7B.

Figure 9:
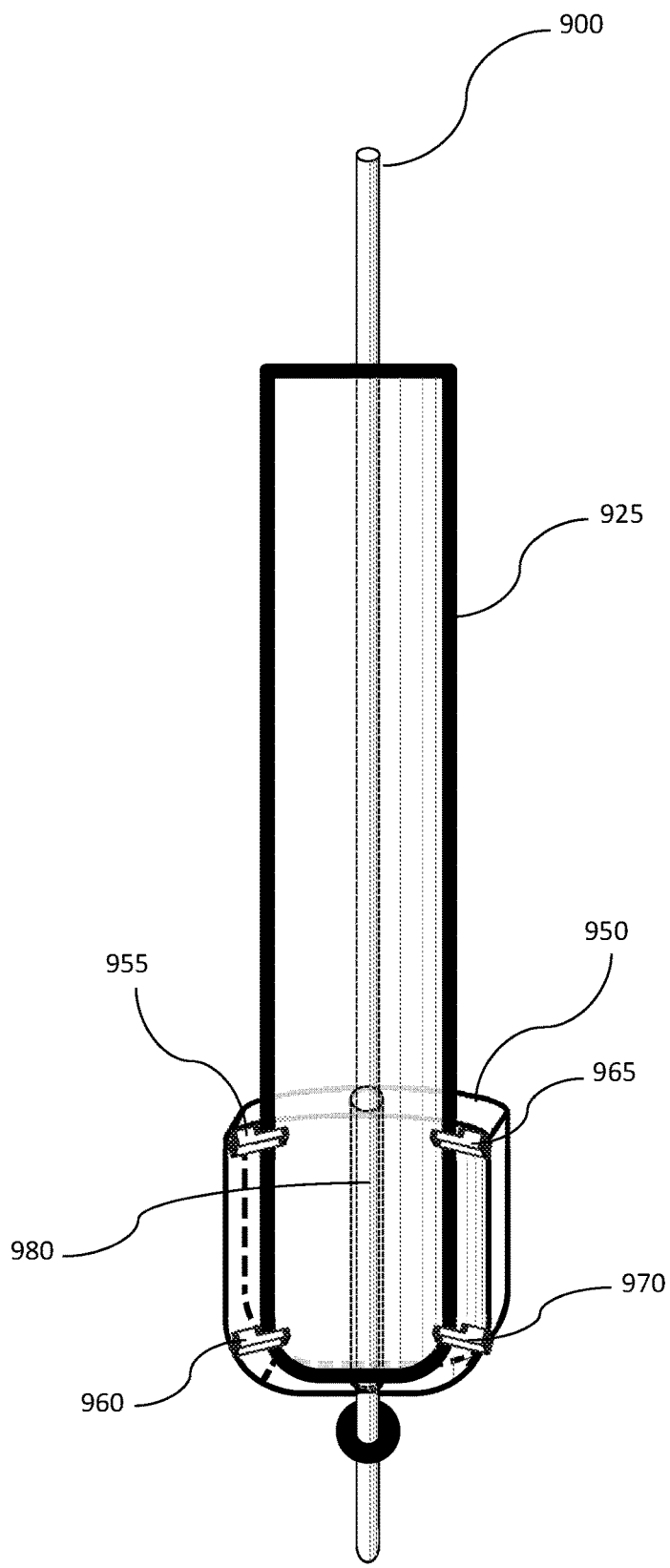
FIG. 9 depicts a depicts a shorter retractor blade with a tubular slot mounted on a probe, attached to a longer retractor blade that does not have a tubular slot in accordance with an illustrative embodiment.

FIG. 9 depicts a retractor blade 925 connected to a retractor blade attachment 950, with the retractor blade attachment 950 having a tubular slot 980 that accommodates a probe 900 in accordance with an illustrative embodiment. The retractor blade 925 is secured to the retractor blade attachment 950 through connections points 955, 960, 965, and 970.

Figure 10:
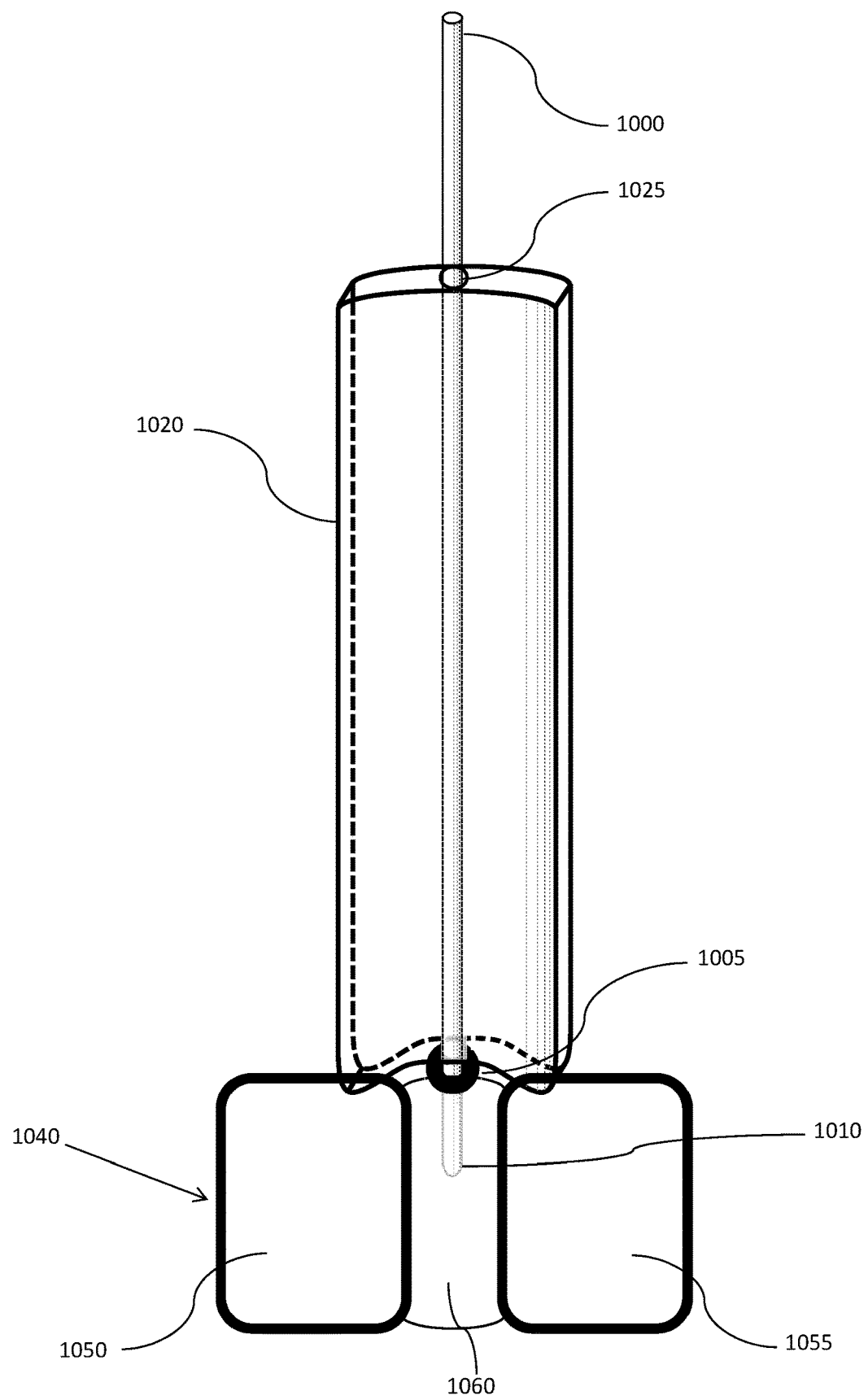
FIG. 10 depicts a retractor blade mounted on a probe that has been anchored in a lumbar vertebral disk, in accordance with an illustrative embodiment

FIG. 10 depicts a retractor blade 1020 with a tubular slot 1025, a probe 1000, and a vertebral segment 1040 in accordance with an illustrative embodiment. The standard lateral retroperitoneal approach is performed, and the psoas muscle identified and mobilized posteriorly. The probe 1000 has a pointed tip 1010 and is inserted and docked in the intervertebral disk 1060. The intervertebral disk 1060 is located between vertebral bodies 1050 and 1055 and these three structures comprise the vertebral segment 1040. The probe 1000 has a collar 1005 that is flush with the lateral aspect of the intervertebral disk 1060. The collar 1005 controls the depth of probe insertion by coming into contact with the disk and preventing further probe advancement, and also allows for fluoroscopic or other intra-operative imaging determination of probe location with respect to the disk 1060. Once the probe 1000 is docked in the disk 1060 in the desired location based on direct visualization and fluoroscopic or other intra-operative imaging, the retractor blade 1020 is placed onto probe 1000 via tubular slot 1025 which accommodates probe 1000, and the retractor blade 1020 is slid down the probe 1000 until the leading edge of the retractor blade 1020 comes into contact with the intervertebral disk 1060 and adjacent vertebral bodies 1050 and 1055. The probe 1000 is contained within the tubular slot 1025 and thus serves to both guide the retractor blade 1020 into the desired position and then to hold the retractor blade 1020 in this position by virtue of being anchored in the intervertebral disk 1060. The retractor blade may be optionally attached to a table-mounted expandable tubular retractor, and then the fusion proceeds in the standard manner.

Figure 11:
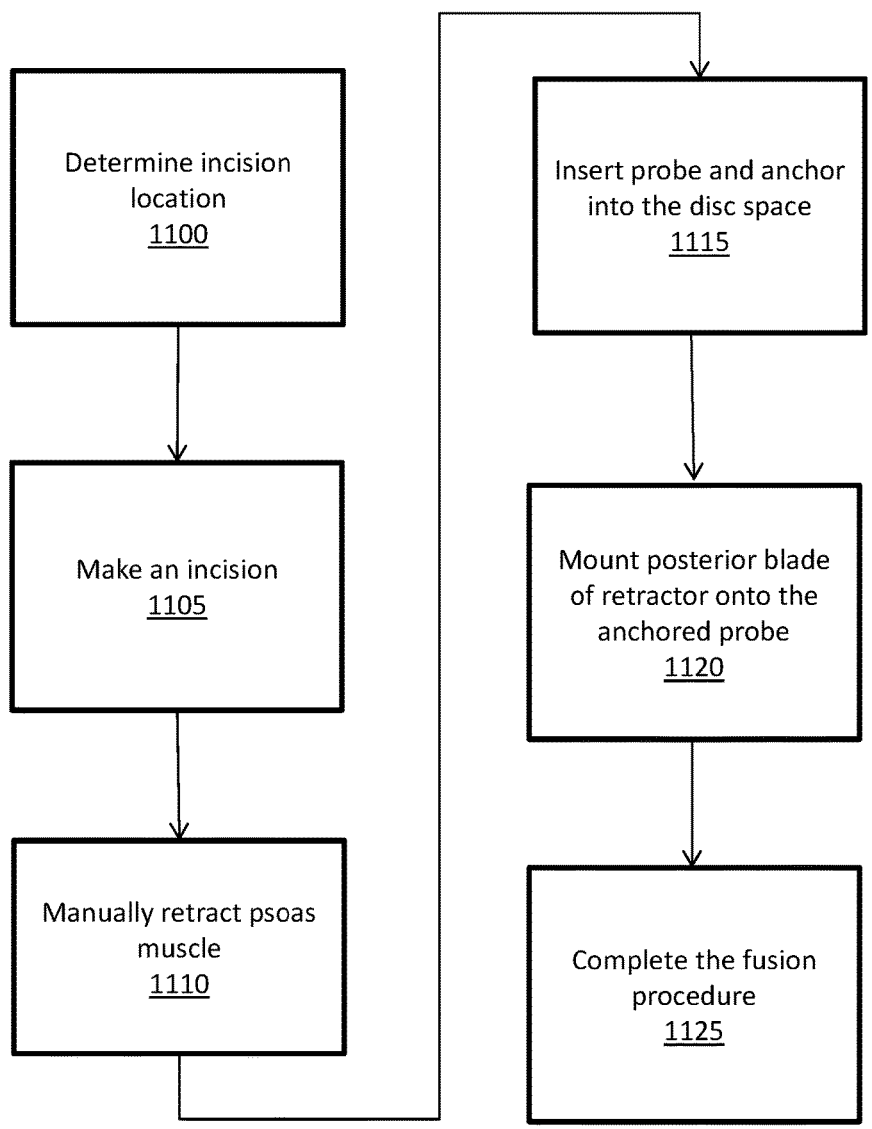
FIG. 11 is a flow diagram depicting a process for performing a lumbar spine fusion in accordance with an illustrative embodiment.

FIG. 11 is a flow diagram depicting a process for performing a lumbar spine fusion in accordance with an illustrative embodiment. In alternative embodiments, fewer, additional, and/or different operations may be performed. Additionally, the use of a flow diagram is not meant to be limiting with respect to the order of operations performed. In an operation 1100, the surgeon determines an incision location. In an illustrative embodiment, the incision location is determined with the use of fluoroscopy. Alternatively, any other method(s) known to those of skill in the art may be used. In an operation 1105, the surgeon makes an incision at the determined incision location.

In an operation 1110, the surgeon accesses and manually retracts the psoas muscle. As discussed herein, once the anterior border of the psoas muscle is identified visually, the psoas muscle is carefully mobilized posteriorly to reveal the disk space. Once the disk is identified, a handheld retractor can be used to carefully retract the psoas muscle in its entirety posteriorly to further expose the disk. In an operation 1115, a probe is inserted into and thus anchored in the disk space. In an illustrative embodiment, the probe is the probe 100 described with reference to FIG. 1.

In an operation 1120, the surgeon mounts a posterior blade of a retractor onto the anchored probe. In an illustrative embodiment, the posterior blade of the retractor includes a slot that is configured to receive a portion of a shaft of the probe, as illustrated and described with reference to FIG. 5. As noted above, another portion of the shaft of the probe is already anchored into the disk space. In an operation 1125, the surgeon completes the fusion procedure as known to those of skill in the art.

The components described herein can be made in a variety of lengths and/or shapes to accommodate various patient anatomies and surgeon preferences. The components can be made from stainless steel, titanium, titanium-alloy, cobalt-chrome, or any suitable material that is able to withstand the biomechanical stresses under which they will be placed.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A retractor blade attachment system comprising:
   a probe that includes a shaft and a pointed tip, wherein pointed tip is configured to puncture tissue in a disk space of a disk and anchor the probe to the tissue;
   a collar on the probe, wherein the collar is configured to act as a stop to control a distance through which the shaft of the probe traverses the tissue;
   a fastener configured to secure the collar to the shaft such that the collar is slidably mounted to the shaft; and
   a retractor blade attachment, wherein the retractor blade attachment includes
      a slot configured to receive at least a portion of the shaft of the probe; and
      one or more connections configured to secure the retractor blade attachment to a retractor blade.

2. The retractor blade attachment system of claim 1, wherein the retractor blade attachment further comprises an end portion, and wherein at least a portion of the end portion is configured to rest upon one or more of the collar and the disk when the retractor blade attachment is mounted on the probe.

3. The retractor blade attachment system of claim 2, wherein the end portion of the retractor blade attachment is concave.

4. The retractor blade attachment system of claim 2, wherein the end portion of the retractor blade attachment is convex.

5. The retractor blade attachment system of claim 1, wherein the one or more connections comprise one or more clips configured to secure one or more edges of the retractor blade.

6. The retractor blade attachment system of claim 5, wherein the one or more clips comprise spring loaded clips.

7. The retractor blade attachment system of claim 5, wherein the one or more clips are detachable.

8. The retractor blade attachment system of claim 1, wherein the slot of the retractor blade attachment is a tubular slot.

9. The retractor blade attachment system of claim 8, wherein the tubular slot is positioned within a wall of the retractor blade attachment.

10. The retractor blade attachment system of claim 1, wherein the slot of the retractor blade attachment is a partially open slot.

11. The retractor blade attachment system of claim 1, wherein the slot of the retractor blade attachment is mounted at least partially posterior to the retractor blade.

12. The retractor blade attachment system of claim 1, wherein the slot of the retractor blade attachment is mounted at least partially anterior to the retractor blade.

13. The retractor blade attachment system of claim 1, wherein the one or more connections comprise 4 connectors.

\* \* \* \* \*